(12) United States Patent
Purdie et al.

(10) Patent No.: US 6,737,275 B2
(45) Date of Patent: May 18, 2004

(54) DIRECT SERUM LIPIDS ASSAYS FOR EVALUATION OF DISEASE STATES

(75) Inventors: Neil Purdie, Stillwater, OK (US); Justin A. Krouse, Langhorne, PA (US); Joe Studer, Stillwater, OK (US); Adrian D. Marais, Cape Town (ZA)

(73) Assignees: The Board of Regents for Oklahoma State University, Stillwater, OK (US); University of Cape Town, Rondebosch (ZA)

( * ) Notice: Subject to any disclaimer, the term of this patent is extended or adjusted under 35 U.S.C. 154(b) by 44 days.

(21) Appl. No.: 10/068,305

(22) Filed: Feb. 5, 2002

(65) Prior Publication Data

US 2002/0160519 A1 Oct. 31, 2002

Related U.S. Application Data

(60) Provisional application No. 60/266,541, filed on Feb. 5, 2001.

(51) Int. Cl.$^7$ .................... G01N 33/92; G01N 21/31
(52) U.S. Cl. .................... 436/71; 436/164; 436/171
(58) Field of Search .................... 436/13, 71, 164, 436/171, 172

(56) References Cited

U.S. PATENT DOCUMENTS

| | | | |
|---|---|---|---|
| 3,705,181 A | * 12/1972 | Parikh et al. | 552/526 |
| 3,884,638 A | * 5/1975 | Dixon et al | 436/71 |
| 3,960,493 A | * 6/1976 | Beitz et al. | 436/22 |
| 4,328,000 A | * 5/1982 | Horn et al. | 436/86 |
| 4,360,470 A | * 11/1982 | Batcho et al. | 552/548 |
| 4,486,531 A | * 12/1984 | Ziegenhorn et al. | 435/19 |
| 4,626,511 A | * 12/1986 | Artiss et al. | 436/8 |
| 4,701,417 A | * 10/1987 | Portenhauser et al. | 436/13 |
| 4,814,508 A | * 3/1989 | Gors et al. | 568/309 |
| 4,883,765 A | * 11/1989 | Tamir et al. | 436/71 |
| 5,021,197 A | * 6/1991 | Takeda et al. | 558/271 |
| 5,101,049 A | * 3/1992 | Goda et al. | 549/71 |
| 5,168,067 A | * 12/1992 | Miller et al. | 436/71 |
| 5,593,894 A | 1/1997 | Purdie | 436/71 |
| 5,989,916 A | 11/1999 | Purdie | 436/13 |

FOREIGN PATENT DOCUMENTS

| | | | |
|---|---|---|---|
| GB | 1385320 | 2/1975 | G01N/31/14 |
| WO | WO 89/02925 | 4/1989 | C12Q/1/00 |
| WO | WO 96/04556 | 2/1996 | G01N/33/53 |

OTHER PUBLICATIONS

Groves, J.K. "The Friedel–Crafts Acylation of Alkenes." *Chemistry Society Review.* vol. 1, 1972, pp. 73–97.

Katan, Martijn B., Frits van der Haar, Daan Kromhout, and Frans J. M. Schouten. "Standarization of Serum Cholesterol Assays by Use of Serum Calibrators and Direct Addition of Liebermann–Burchard Reagent." *Clinical Chemistry.* vol. 28, No. 4, 1982, pp. 683–686.

Miettinen, T.A., V. Naukkarinen, J.K. Huttunen, S. Mattila, T. Kumlin. "Fatty–acid composition of serum lipids predicts myocardial infarction." *British Medical Journal.* vol. 285, 1982, pp. 993–996.

Vass, L., "Eine einfache und zuverlässige Methode zur Bestimmung des Gesamtcholesterols im Blutserum" *Clinica Chimica Acta.* vol. 45, 1973, pp. 313–315.

Zoppi, Francesco. "Single Cuvet Sequential Determination of Triglyceride and Cholesterol." *Clinical Chemistry.* vol. 31, No. 12, 1985, pp. 2036–2039.

* cited by examiner

*Primary Examiner*—Jeffrey R. Snay
(74) *Attorney, Agent, or Firm*—Fellers, Snider, Blankenship, Bailey & Tippens, P.C.

(57) ABSTRACT

The invention presents a method designed to simultaneously measure certain unsaturated lipids and certain vitamins present either as single substances or in complex mixtures such as exist in serum and natural oils. Target lipids are free cholesterol, unsaturated cholesteryl esters; free polyunsaturated fatty acids, and their esters as triglycerides, and phospholipids. Distributions of these analytes over the broad range of serum lipoproteins from chylomicrons to high density fractions are determined using a procedure that involves a single step reaction in which the molecular unsaturations are subjected to non-enzymatic color inducing reagents. For natural oils and vitamins, the same method serves as a quality control procedure. Analytical detection is achieved using broad spectrum absorbance and/or fluorescence measurements. Measured spectra are aggregates of the absorbance contributions from each of the analytes. Data analyses follow two paths. One uses raw spectral data. In the other, multivariate methods of analysis, particularly principal component (or factor) analysis, leads to 2-D and 3-D clustering correlations which have significant diagnostics capabilities for the early detection of human serum disorders and for quality control.

15 Claims, 13 Drawing Sheets

DIRECT SERUM LIPIDS ASSAYS FOR EVALUATION OF DISEASE STATES

CROSS REFERENCE TO RELATED APPLICATION

This application claims benefit of U.S. provisional patent application Serial No. 60/266,541, filed Feb. 5, 2001, the disclosure of which is incorporated herein by reference.

BACKGROUND OF THE INVENTION

In U.S. Pat. Nos. 5,593,894 and 5,989,916, incorporated herein by reference, speciation of serum cholesterol over the very low density lipoprotein (VLDL), low density lipoprotein (LDL), and high density lipoprotein (HDL) fractions was done in a direct manner based upon a multivariate analysis treatment of visible absorbance data produced by simultaneous color derivatizations of the serum cholesterol lipoprotein subfractions. Total serum cholesterol (TC) was determined as the sum of the amounts in each fraction.

The preferred procedure, as presented in the above referenced patents, for the direct assay of cholesterol was to react a 10 $\mu$L aliquot of serum with 1.0 mL of a reaction mixture comprised of an acylating compound having the general formula $R.CO.R_1$, wherein $R_1$ is halogen, R is selected from the group of lower alkyl radicals, and a predetermined amount of perchlorate ion effective enough to form a spectrophotometrically active product with cholesterol. The perchlorate was selected from a group consisting of barium perchlorate, zinc perchlorate, and perchloric acid. For the preferred acylating compound the R group was methyl, the $R_1$ was chloride ion, and the preferred perchlorate was either $HClO_4$ or $Zn(ClO_4)_2.6H_2O$. Three spectral detection methods (absorbance, fluorescence, and circular dichroism) were described as being suitable for the measurement of the color intensity as a function of wavelength after a fixed time (usually 15 minutes). Absorbance detection was the preferred choice.

The choice of an acetyl chloride with either perchloric acid or zinc perchlorate hexahydrate reagent constitutes only one of many. Alternative reagent mixtures, not addressed in earlier patents, convey similar information for cholesterol and, in certain cases, additional information for other serum lipids besides cholesterol in a single simultaneous test. Alternative reagent compositions are specified in detail in this disclosure as are some options where added modifiers, in particular glacial acetic acid and acetic anhydride, can enhance the spectral data and give better control over the experimental reproducibility.

Data analyses claimed in U.S. Pat. Nos. 5,593,894 and 5,989,916 were limited to the simultaneous assays of three cholesterol variables, namely VLDL-C, LDL-C, and HDL-C, using absorbance data at only five wavelengths and the single reagent system, acetyl chloride and $HClO_4$ catalyst. TC values were calculated as the sums of the parts.

Implications that other serum lipids (e.g. triglycerides and free fatty acids) are involved in the genesis of coronary heart disease (CHD), and appear to react with the same derivatizing reagent, stimulated the need for developing broader simultaneous assays of multiple variables but still using a single experimental procedure.

SUMMARY OF THE INVENTION

1. Objects

The object of the present invention is to expand the diagnostic capabilities of the technology from being only a serum cholesterol lipoprotein profile to a much broader serum lipids assay. The focus is on serum (or plasma) cholesterol and its analogs, and on serum (or plasma) long chain fatty acids (LCFA's) that are present either as free acids or as esters of cholesterol, glycerol, and phospholipids. Esters are the predominant forms for LCFA's in blood. Amounts of free acid forms of LCFA's are, in general, very small. Taken altogether, the assay of each individual analyte would constitute a comprehensive screening of serum lipids from a single experimental test.

LCFA's, and their ester derivatives, are both saturated and unsaturated. In natural forms the sites of unsaturation are cis-ethylenic double bonds, i.e. —CH=CH—. The number of double bonds ranges from one, for a series of monounsaturated fatty acids (MUFA's), of which oleic acid is the predominant example, to polyunsaturated fatty acids (PUFA's), represented by linoleic acid with 2 and eicosohexaenoic acid with 6 all cis- double bonds.

2. Extended Lipid Analyses

It was determined that the chromogenic acylating reagent (s), originally thought to be selective to only cholesterol, is also selective towards particular —CH=CH— double bonds that are present in both cyclic and open chain aliphatic molecular structures. In serum, therefore, the actual number of lipid analytes that do react with the acylating reagent is extended to include free cholesterol (FC); saturated and unsaturated cholesteryl-LCFA esters (CE); free LCFA's themselves; and LCFA's in the form of triglycerides (TG) and phospholipids (PL), both of which are unsaturated LCFA esters of glycerol. Saturated LCFA's do not react.

A red color, which is typical for standard reference materials (SRM's) for FC and CE, is a product of reactions with the $\Delta^5$ carbon—carbon double bond in ring B of the steroid structure. Colors from reactions with carbon—carbon double bonds in SRM forms of open chain LCFA's, in contrast, are yellow to pale orange. When SRM forms of cholesterol and LCFA are mixed and reacted in vitro, the color is an aggregate of red and yellow with the shade of orange being determined by the proportions of each component and the relative absorbance intensity of each chromophore in the products from the simultaneous acylations.

Every one of the colored products from the reactions with cholesterol analogs and PUFA analogs fluoresces. Emission fluorescence spectroscopy is an alternative detector to absorbance although less easy to use and interpret.

These same primary lipids occur in serum where they are distributed over the chylomicron, VLDL, IDL, LDL, and HDL lipoprotein fractions and subfractions, in different proportional amounts. These lipids together with apolipoproteins and other lesser components in variable amounts, determine the relative densities of the individual lipoprotein particles which is a common basis for their physical distinctions. Colors observed from acylations of synthetically prepared serum lipoprotein fractions, progress from being predominantly yellow (chylomicrons) through orange (VLDL, IDL) to pink (LDL, HDL), as the LCFA amounts decrease and the cholesterol amounts increase.

An analogous color variation is seen to occur for acylations of synthetic mimics of the Type I, IIa, IIb, III, IV, and V dyslipidemias. On the basis of quantitative interpretative analysis of the absorbance spectra associated with the resultant aggregate colors for these mixtures, the opportunity is presented to determine the amounts of each individual lipid in real serum samples with the same dyslipidemic designations.

3. Assay Procedure

The assay procedure of the present invention is performed in three general steps:

subject the lipids in a small volume aliquot of serum (plasma) to simultaneous selective acylations using a preferred color inducing reagent;

measure absorbance and/or fluorescence spectral data for the colored products over the entire visible wavelength range using a fast scanning spectrophotometer or spectrofluorimeter;

determine the amount of each lipid, and/or the proportionate amount of each lipoprotein particle in the serum lipid profile using a combination of multiple wavelength detection with modern multivariate statistical analyses methods.

4. Object of the Invention

While there have been other attempts to routinely measure total serum cholesterol and total TG in a simultaneous assay, there have been none where the focus of the assay was on either the total unsaturated lipids or the discrimination between cholesteryl and glyceryl based esters.

Although all serum lipoprotein fractions are composed from the same, relatively few, fundamental lipids, and differ only in their relative proportions in each lipoparticle, there is more than sufficient evidence from the subtle differences observed in the multiplexed spectral data to believe that a clinical diagnostic procedure has been developed that discriminates among the different serum dyslipidemias and diabetes. Its ultimate proof will depend upon the creation of a comprehensive library of spectral data for as broad a cross section of the general population as possible. The library will have sufficient number representations from normal and all forms of abnormal lipidemias and be a comprehensive resource from which can be derived more dependable, and more meaningful, risk factor models for the early assessment and prediction of coronary heart disease (CHD) and diabetes.

DETAILED DESCRIPTION OF THE PREFERRED EMBODIMENT

Chemistry of the Color Reaction

Introduction

Figure 1:
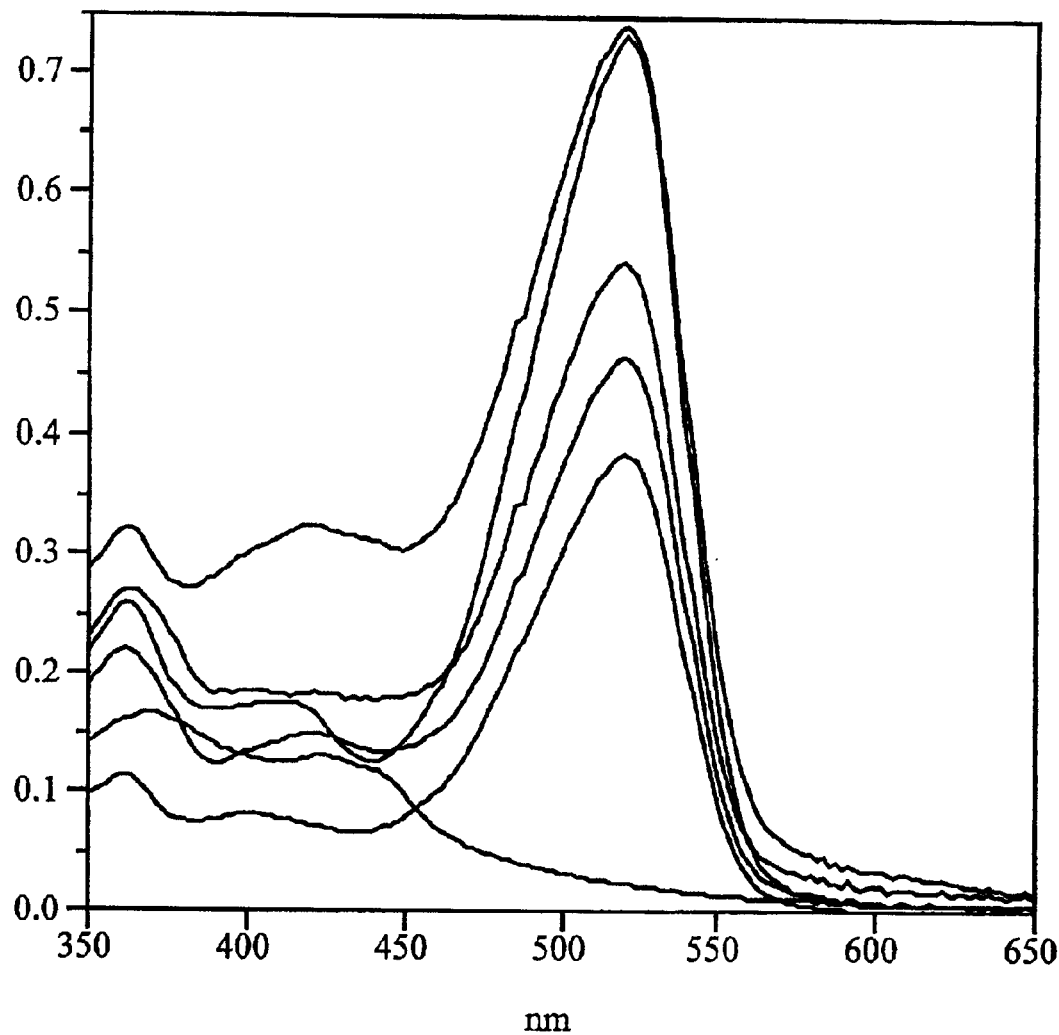
FIG. 1. Absorbance spectra for a series of unsaturated lipids where the color inducing reagent is AC+70% perchloric acid. In order of decreasing intensity at 520 nm, the unsaturated lipids are: cholesteryl arachidonate; free cholesterol; serum; cholesteryl linoleate; cholesteryl myristate; and glyceryl trilinoleate (a TG mimic).

It is submitted that any Friedel-Crafts (F-C) acylating reaction, catalyzed by the addition of any Lewis or Bronsted acid, could conceivably be used to produce colored products when reacted with SRM's of cholesterol and PUFA analogs. Historically the preferred acylating agents are glacial acetic acid, acetic anhydride, acetyl chloride, and benzoyl chloride; the preferred Lewis acids are ions Al, Sn, Ba, and Zn; and the preferred Bronsted acids are the mineral acids HCl, $HClO_4$, $HNO_3$, $H_2SO_4$, and $H_3PO_4$.

1. Mechanism

The mechanism of the color inducing reaction described in the incorporated prior patents, in which the reagents are acetyl chloride, $CH_3CO.Cl$, and a Lewis acid (zinc or barium perchlorate) fits the literature description of a F-C acylation reaction. Under certain reaction conditions the $CH_3CO\bullet$ radical will replace hydrogen from alcohol (—OH) and amine (—$NH_2$) functional groups with the elimination of HCl. Acylation protects terminal amine groups in peptides and proteins, prior to their separation by HPLC. As a general rule these acylations do not produce colored products.

Under different experimental conditions the $CH_3CO\bullet$ radical and the $Cl^-$ ion can be made to add across a carbon—carbon double bond (—CH=CH—). For this to occur, however, at least one methylene (—$CH_2$—) group must be in a position that is $\alpha$ to the double bond. The minimum molecular structural requirement for the reaction to occur, therefore, is (—CH=CH—$CH_2$—). It is speculated that a free radical is produced at the carbon of the methylene group that initiates a subsequent propagation reaction leading to extended conjugation and colored chromophores that absorb energy in the visible spectral range, detectable by absorbance, fluorescence, and circular dichroism. A totally conjugated polyene structure would not react by this proposed mechanism since the necessary methylene group is not present.

For FC under the appropriate reaction conditions, acylation would occur at the —OH group in the 3β-position, and at the $\Delta^5$-double bond that is adjacent to a —$CH_2$— group in the B-ring. In support of this contention, sitosterol and stigmasterol, both $\Delta^5$-plant sterols, were the only two from a wide selection of twenty or more possible interfering steroidal molecules that produced an analogous color reaction. Other biologically important compounds that react to produce a color are the A, $D_3$, and K vitamins, which are present in such small quantities in serum to be below their detection limits.

For 3β-saturated cholesteryl esters, e.g. laurate, myristate, pelargonate, stearate, etc., only the $\Delta^5$-double-bond is acylated. The assay will not detect saturated acids.

For 3β-MUFA and PUFA esters of cholesterol, e.g. oleate, linoleate, linolenate, arachidonate, eicosopentaenoate, eicosohexanoate, etc., acylations occur at the $\Delta^5$-double bond of the cholesteryl moiety and at all of the —CH=CH—$CH_2$— groups in the LCFA's.

These same LCFA's form esters with glycerol and are majority components in the molecular structures of serum TG and PL. In general, natural forms of the acids are all cis-isomers. trans-isomers are introduced to blood through dietary pathways. In TG at least one of the three LCFA ester groups is unsaturated. PL are also triesters, two of which are LCFA esters, saturated and/or unsaturated. The third ester grouping in PL is one of several substituted mono-phosphatidyl esters of glycerol that include choline, inositol, and serine. Even if they react, these non-LCFA substituents do not produce a colored product.

Double bonds in naturally occurring PUFA esters are generally unconjugated and increase in number as the number of carbon atoms in the LCFA chain increases, one for oleate, two for linoleate (or ω-6 FAE), and its trans-isomer linolaiate, three for linolenate (or ω-3 FAE) and its conjugated geometric isomers, four for arachidonate, and five and six for the eicoso-derivatives respectively. On average PUFA esters amount to almost 87% of the total LCFA's in serum TG. In the context of serum lipids assays therefore, oleate, linoleate, and linolenate and, to lesser amounts, higher conjugated and higher unconjugated PUFA esters of TG and PL in serum, are susceptible to acylation by the second mechanism.

The high incidence of oleic, linoleic, and linolenic esters in natural vegetable oils makes them accessible to quality control testing using the same reagents and assay procedures.

2. Alternative Acylating Agents

Glacial acetic acid (GAC), acetic anhydride (AAH), and acetyl chloride (AC) are three suitably safe acylating reagents for routine reactions with cholesterol and PUFA analogs. The acylating "strength" increases in the order GAC<AAH<AC. The second essential ingredient is the acid whose function is believed to be catalytic since it is present in non-stoichiometric proportions.

The preferred reagent(s) identified in the incorporated references are:

(a) AC+70% perchloric acid, and (b) AC+zinc perchlorate hexahydrate.

These can be classified by the nature of their acids as Bronsted and Lewis acid reactions respectively.

Other reagents that function almost as well and, in one instance at least, perhaps even better than (a) and (b), include the following:

(c) AC+1,2-dichloroethane+70% perchloric acid (d) AC+concentrated sulfuric acid (e) AC+methanesulfonic acid (f) AC+zinc organic acid salts: acetate, gluconate, methoxygluconate (g) AAH+70% perchloric acid (h) AAH+concentrated sulfuric acid (i) AAH+AC+70% perchloric acid (d) AAH+AC+concentrated sulfuric acid.

GAC, by itself, is of insufficient "strength" to acylate the —CH=CH—$CH_2$— groupings. It does however have the valuable asset of causing an ongoing reaction, initiated by AC or AAH, to immediately cease when it is added at, or prior to, the chosen end point time for the color incubation. Spiking with a small aliquot of GAC is recommended whenever emission fluorescence detection is used since data accumulation is slower than it is in absorbance detection.

The mixed acylating reagents (i) and (j) produce a series of absorbance spectra from serum assays that progressively vary with the proportions of AAH to AC. This property could conceivably be manipulated to effectively "separate" the FC/CE absorbance component from the LCFA component as an aid to assaying individual lipid amounts. In routine measurements on serum the two assays would be run in parallel using different reagent compositions. A similar effect is observed for reagent (f) where the spectra for the products vary with the absolute amount of zinc acetate added.

Reactions that involve Lewis acid catalysts bear a resemblance to F-C reactions. Catalysis by Bronsted acids is entirely consistent with the use of concentrated $H_2SO_4$ as a component of the chromogenic Liebermann-Burchard (L-B) reagent (7–9), that typically was a 60:30:10 mixture of GAC, AAH, and concentrated $H_2SO_4$. Until fairly recently the L-B reagent was widely used commercially to determine serum TC. The mixtures used for this invention are safer to use and more stable.

SUMMARY OF ASPECTS OF THE PRESENT INVENTION

1. Molecular Requirements for Color Reactions (1) In the context of being able to produce a color, reagents used for these assays are best described as being selective towards a particular double bond arrangement, that is commonplace in lipids molecules, rather than to only a particular compound, e.g. cholesterol.

(2) A mechanistic requirement of the reaction is that at least one —$CH_2$— group be in a position that is α- to the double bond. The fundamental reactive centers are typically (—CH=CH—CH$_2$—) and (—CH$_2$—CH=CH—CH$_2$—) for unconjugated systems and (—CH$_2$—CH=CH—CH=CH —CH$_2$—) for conjugated systems.

(3) The active functional groups in (3) can be located in either cyclic, e.g. in the B-ring of cholesterol, or in long straight chain aliphatic structures, as they are in LCFA.

(4) The initial step in the color reaction is an acylation that begins with the addition of a CH$_3$CO•$^+$ radical to a C-atom of the double bond. Exact details of subsequent steps are obscure but appear to involve the formation of a free radical on the methylene C-atom followed a progression of propagation steps that lead to a number of poly-unsaturated colored product molecules that have extended conjugations.

2. Acylating Reagents and Reagent Compositions (5) GAC, AAH, and AC were preferred choices taken from a wide selection of potential acylating reagents that also included: benzoyl chloride, palmitoyl chloride, succinyl chloride, cyclohexanyl chloride, chloroethyl-oxoacetate, ethyl-4-chloro-4-oxobutyrate, ethylchloroformate, acryloyl chloride, etc. The others were eliminated for various incompatibility reasons such as insolubility, immiscibility, zero color production, and a too violent reaction on mixing with the water introduced by the acid by an aliquot of serum.

(6) The color reagent, AC+HClO$_4$ (or Zn(ClO$_4$)$_2$) that was claimed to be unique for the assay of serum cholesterol in U.S. Pat. No. 5,989,916, (FIG. 1), is only one of several generic F-C and related acylating reagents that function in analogous ways. Experimental spectral data are included in FIG. 1 for SRM's.

Figure 2:
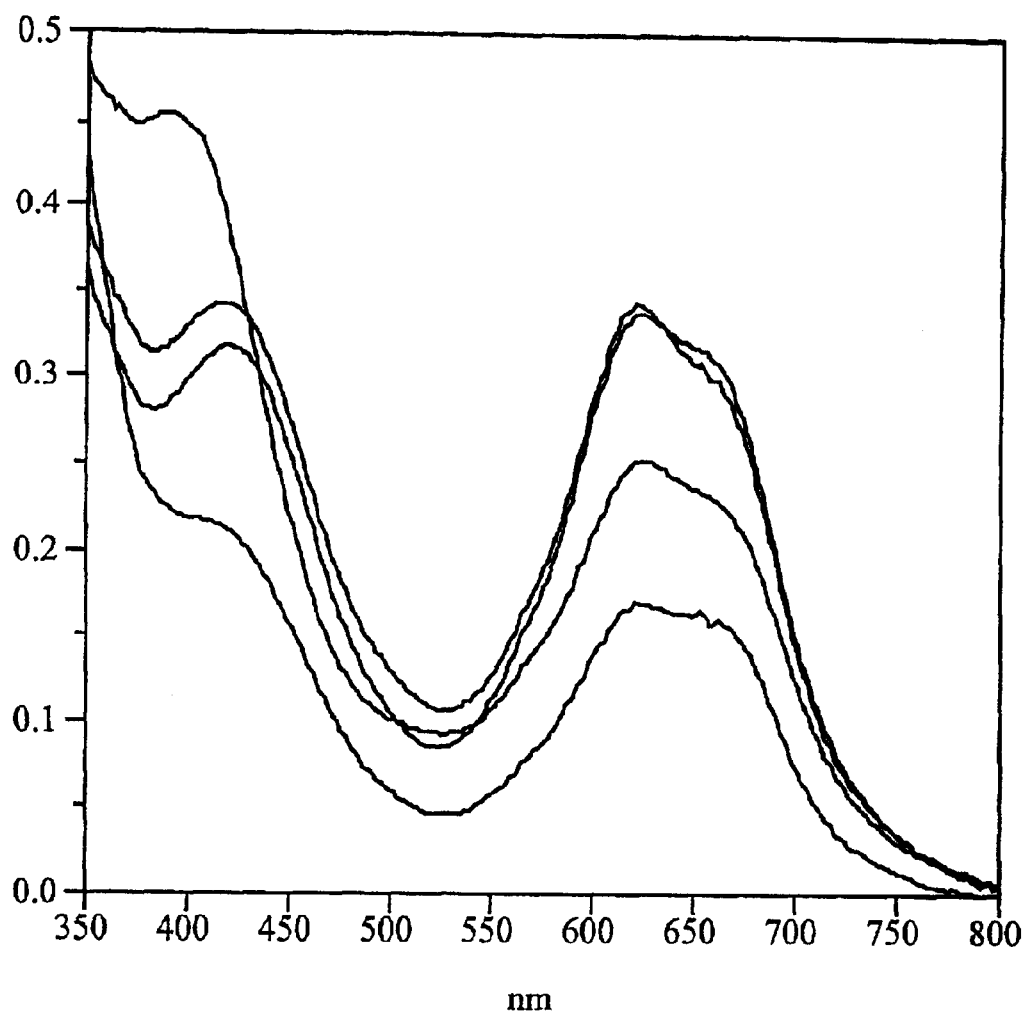
FIG. 2. Absorbance spectra for a series of unsaturated lipids where the color inducing reagent is AAH+concentrated sulfuric acid. In order of decreasing height at 620 nm, the unsaturated lipids are: cholesteryl pelargonate; free cholesterol; serum; and cholesteryl oleate.

(7) In support of the statement in (6), experimental absorbance spectral data are included for products from serum reactions with AAH+H$_2$SO$_4$ (FIG. 2).

Figure 3:
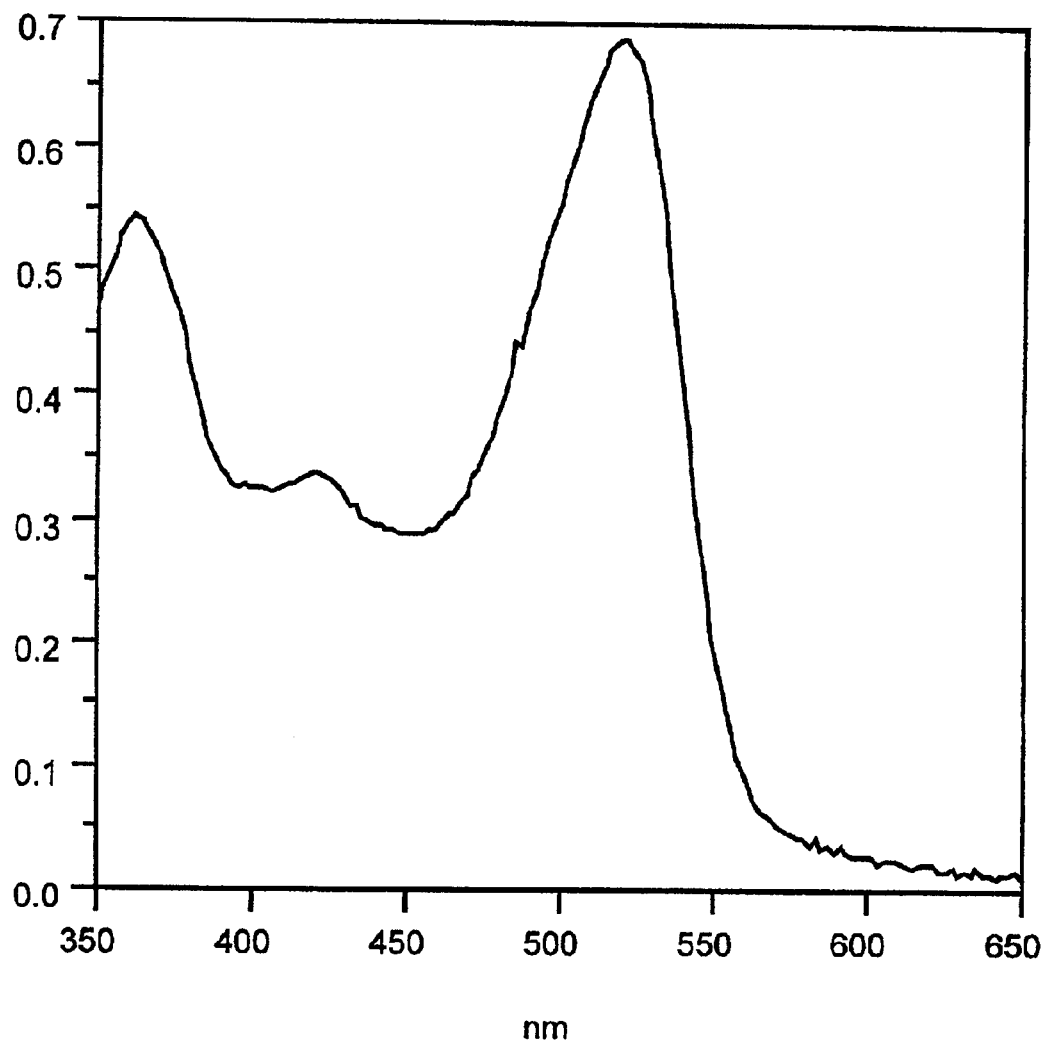
FIG. 3. Absorbance spectrum for a serum sample measured where the color inducing reagent is AC+0.1M zinc acetate.

(9) In support of the statement in (6), experimental absorbance spectral data are included for products from serum reactions with AC+Zn(CH$_3$COO)$_2$ (FIG. 3).

Figure 4:
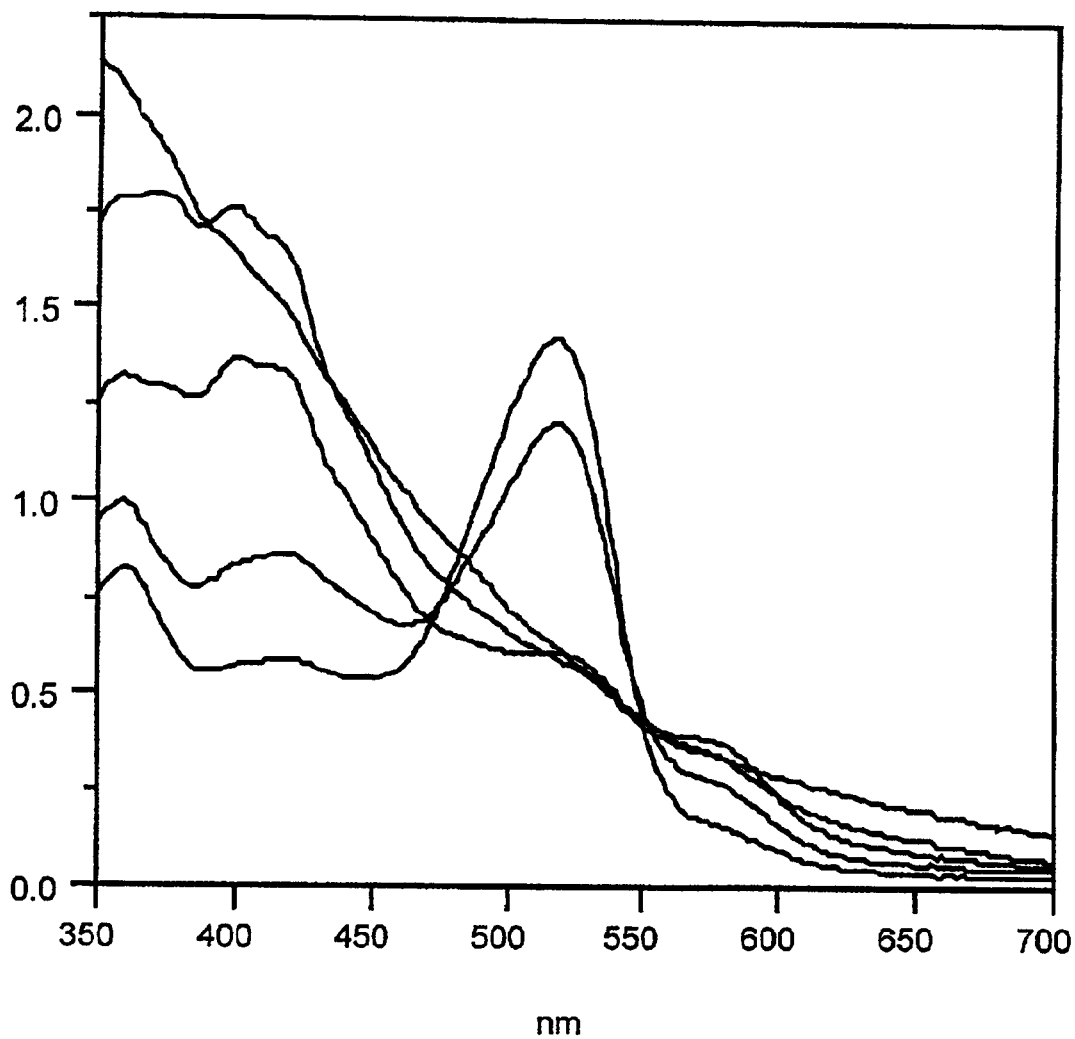
FIG. 4. Absorbance spectra for a single serum sample measured where the color inducing reagent is a series of mixtures of AAH+AC that are 100%, 75%, 50%, 25%, and 0% of AAH from left to right. The catalyst is 70% perchloric acid. As the proportion of AC is increased the absorbance band around 400 nm decreases in intensity and the 520 nm band increases in intensity. Low levels of AC suggest reaction with only PUFA's.

(10) In support of the statement in (6), any of the reagents (b) through (e), listed above, can be modified by adding a third component such as chloroform, 1,2-dichloroethane, and GAC that will provide either better control of the reactions for fluorescence detection, or better discriminations among the analytes (FIG. 4).

Figure 5:
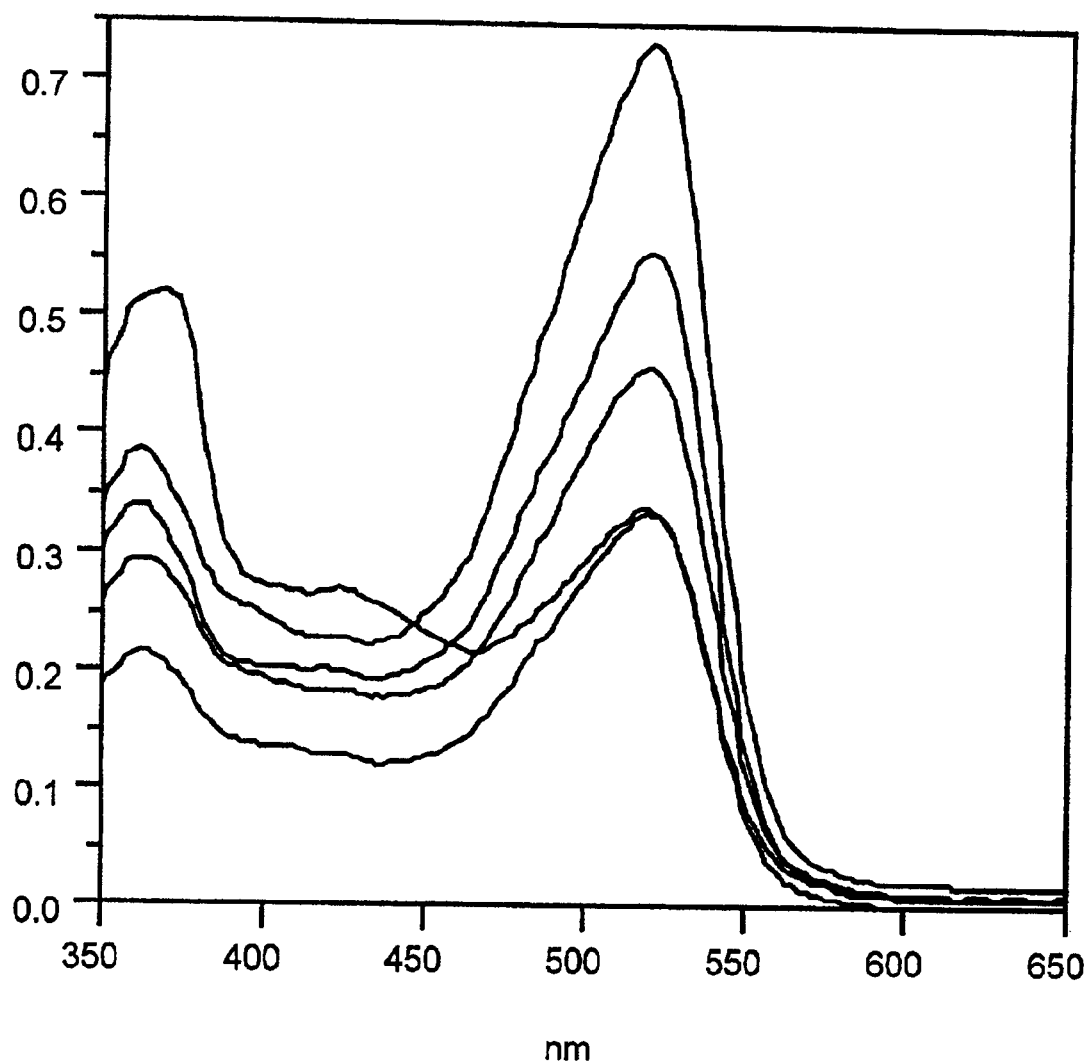
FIG. 5. Absorbance spectra for a series of five serum samples where the color inducing reagent is a 3:2 mixture of AC: 1,2-dichloroethane. The acid catalyst is 70% perchloric acid.

(11) In support of the statements in (6) and (10), experimental absorbance spectral data are included for products from reactions with the ternary reagent AC+AAH+perchloric acid which has the potential to experimentally "separate" the PUFA spectra from the total serum spectra by changing the proportions of acetyl chloride to acetic anhydride (FIG. 5).

(12) Advantages that accrue to using AAH over AC are that the anhydride is less volatile and safer to handle. But more importantly, on their hydrolysis by the water introduced via serum and 70% HClO$_4$, no HCl is evolved.

(13) Advantages that accrue to using the AC+zinc organic acid reagents are that the precipitation of serum proteins and the liberation of HCl gas are both minimal.

3. Spectral Data

(14) For any of the given reagents, the major absorbance bands in the spectra for colored derivatives of SRM's of cholesterol and its esters occur at wavelengths longer than the major bands for colored derivatives of SRM's of MUFA and PUFA's whether they are in the forms of free acids or esters of cholesterol or glycerol. (Table 1).

(15) Significant overlap of the typically cholesterol spectra and the typically LCFA spectra occurs over the spectral range 350–480 nm. It is in this range that the absorbance spectra are most sensitive to changes in the FC, CE and LCFA identities and relative proportions.

Figure 6:
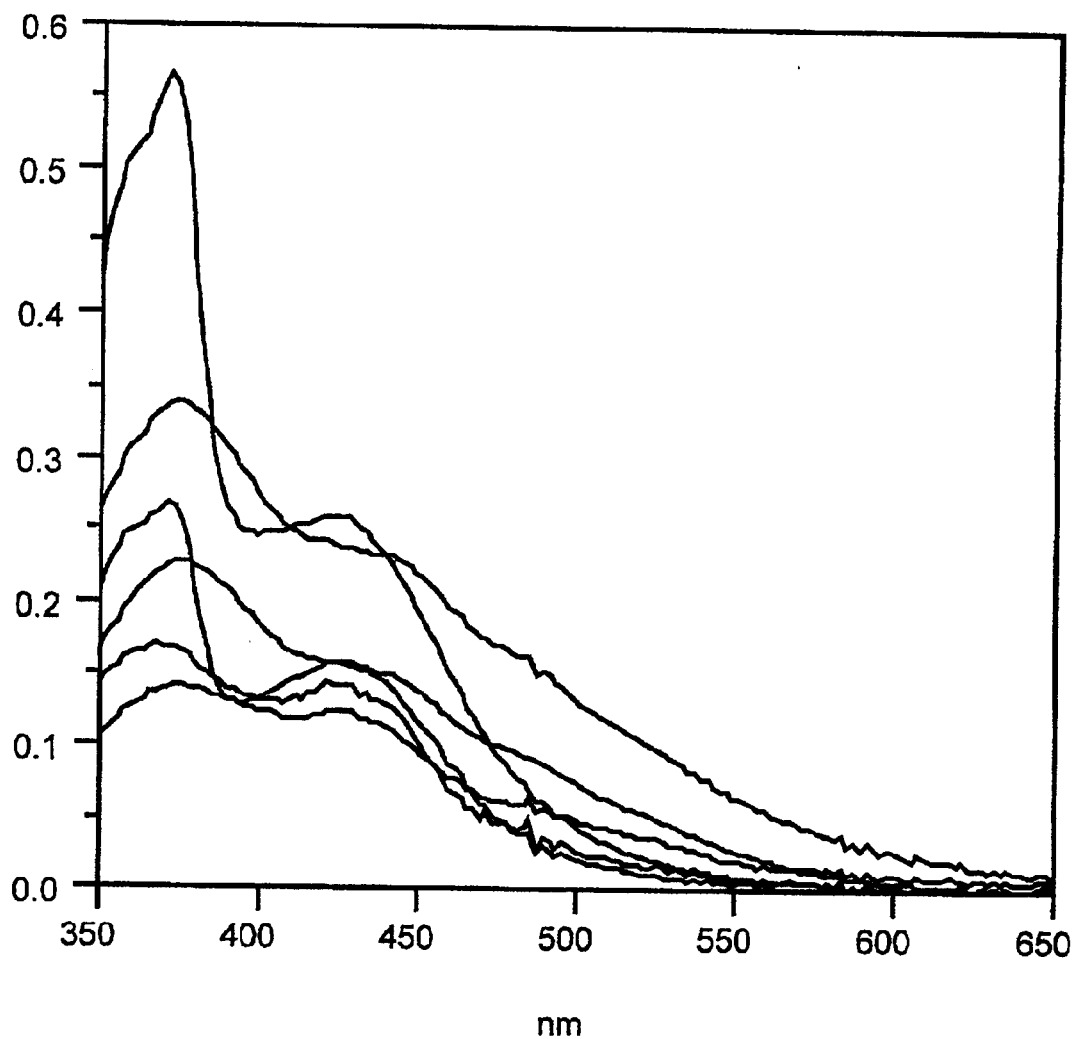
FIG. 6. Absorbance spectra for a series of PUFA methyl esters where the color inducing reagent is AC+70% perchloric acid. In order of decreasing intensity at 375 nm, the PUFA's are: conjugated methyl linoleate; methyl eicosohexa-enoate; methyl linoleate; methyl eicosopentaenoate; methyl linolenate; and methyl arachidonate.

(16) Absorbance spectra for a number of PUFA's including both conjugated and unconjugated isomers of the same LCFA are very characteristic making it possible to distinguish one from the other (FIG. 6).

(17) Absorbance spectra for synthetic mixtures of SRM's of unsaturated lipids are weighted aggregates for the spectra for individual standards.

(18) All of the colored products formed from reactions with all of the acylating reactions fluoresce. Inventive aspects (1) through (17) therefore apply to excitation and emission fluorescence spectral measurements.

(19) The combination of absorbance and fluorescence spectral detection data might expand the discriminatory capabilities of the method without changing the chemistry. Combination of both detectors on a single instrument is a feasible commercial option.

(20) Injection of a small volume aliquot of GAC to the AC reagent mixtures, III.2 (a–f), causes the color reaction to immediately cease. Elimination of further color development gives better control and improved accuracy for spectral measurements, and is especially needed for fluorescence detection.

Figure 7:
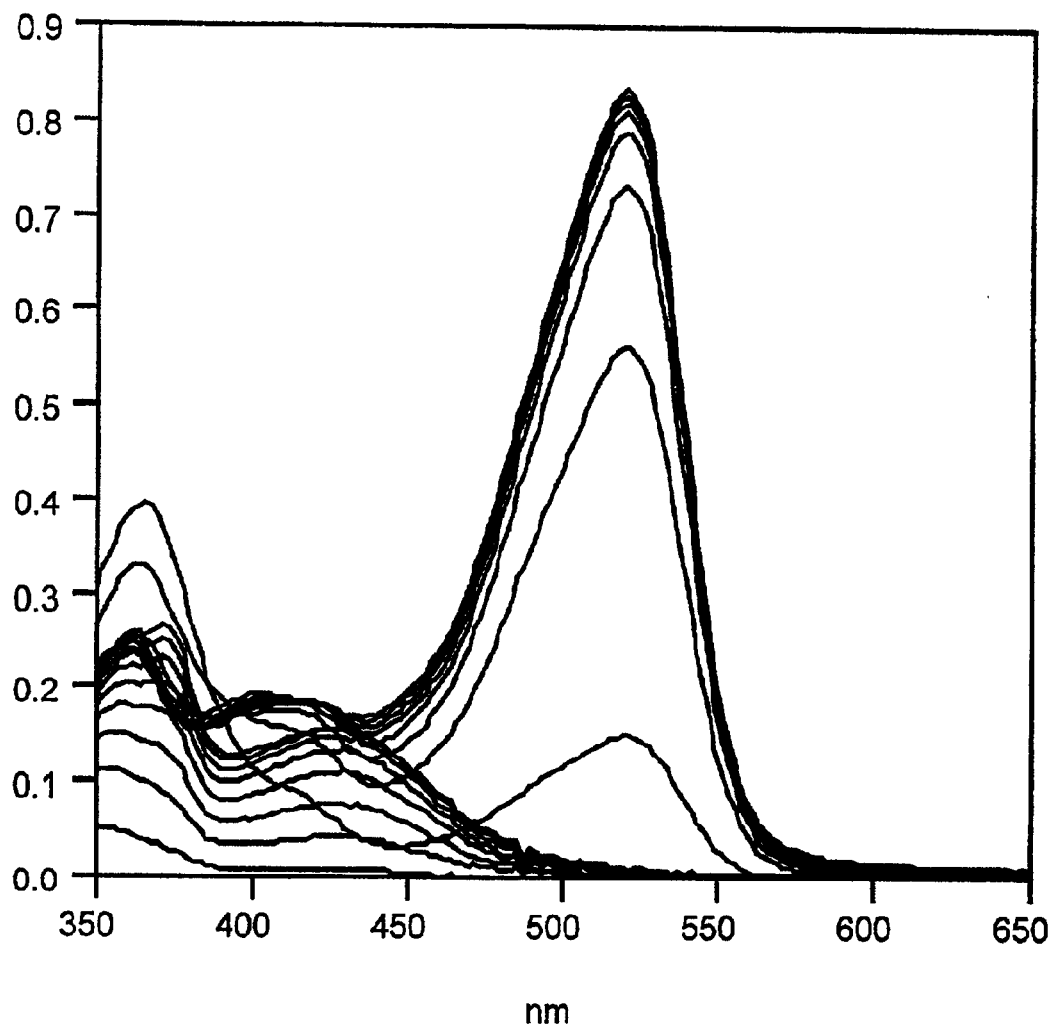
FIG. 7. Absorbance spectra measured at 1 minute intervals up to 15 minutes for free cholesterol (major band maximum at 520 nm) and methyl linoleate (major band maxima at 370 and 410 nm). The reagent is AC+perchloric acid. Absorbance in the 370–410 nm range increases monotonically with time for the methyl linoleate but passes through a maximum value after 3–4 minutes for cholesterol. This difference in behavior simplifies their distinction.

(21) Repeated fast scan absorbance spectral measurements made at one minute intervals, up to and including the end point of the color reaction, produce kinetic data that, with the appropriate treatment, will expand upon the discrimination capabilities of the method without changing the chemistry (FIG. 7).

Figure 8:
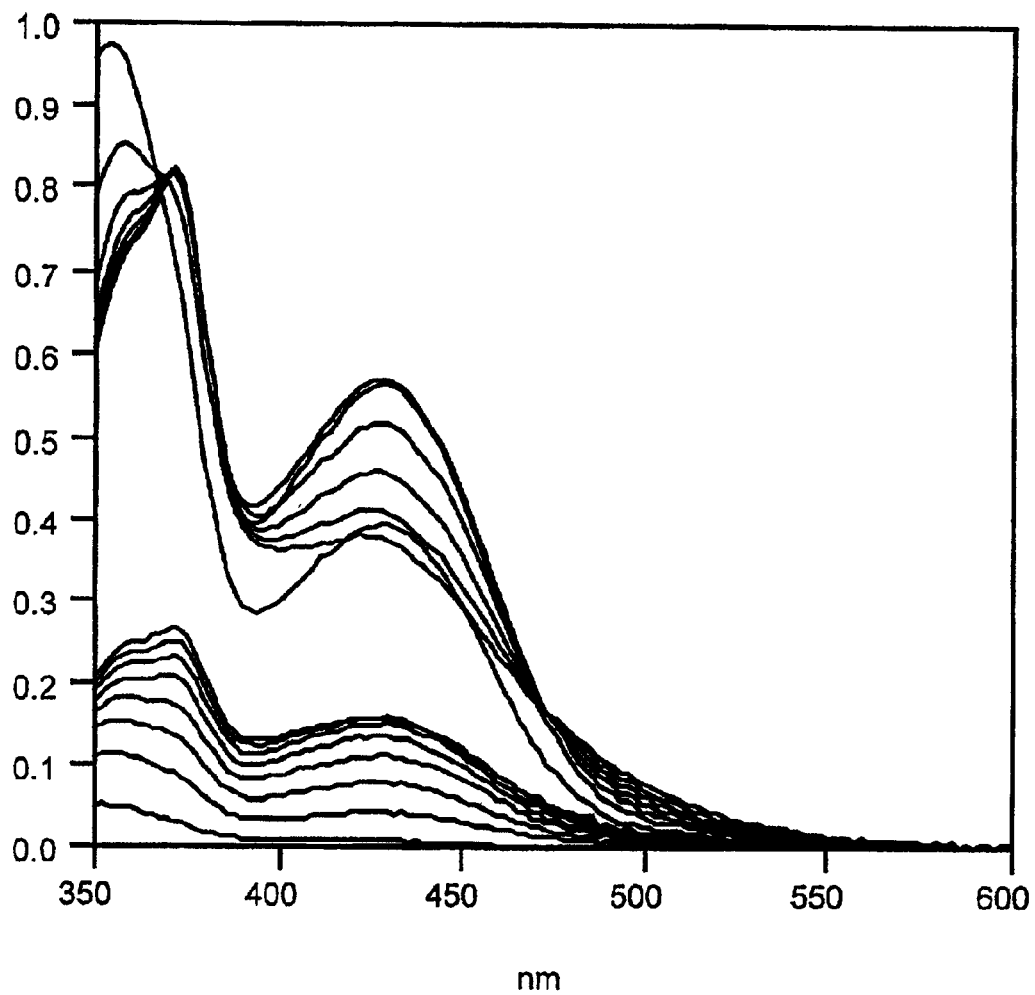
FIG. 8. Absorbance spectra vs. time measured for methyl linoleate (lower series) and for conjugated methyl linoleate (upper series). The catalyst is 70% pechloric acid. The increase is monotonic for the unconjugated ester and non-monotonic for the conjugated ester. This is sufficient evidence to characterize each isomer.

The special attributes that make better discriminations possible are: (i) the rates for LCFA acylations are much faster than the rates for FC and CE acylations; and (ii) during the times taken for colors to develop, absorbances in the range 360–480 nm pass through a maximum value after different times for each lipid. The latter is especially true for conjugated vs. unconjugated lipids (FIG. 8).

4. Spectral Data Analyses and Diagnostic Evaluations (a) Untreated (Raw) Spectral Data

(22) The raw spectrum for a serum sample, or any synthetic mixture, is a permanent snapshot record of the relative proportions of the unsaturated constituents of cholesterol and/or LCFA lipids at a given time.

Figure 9:
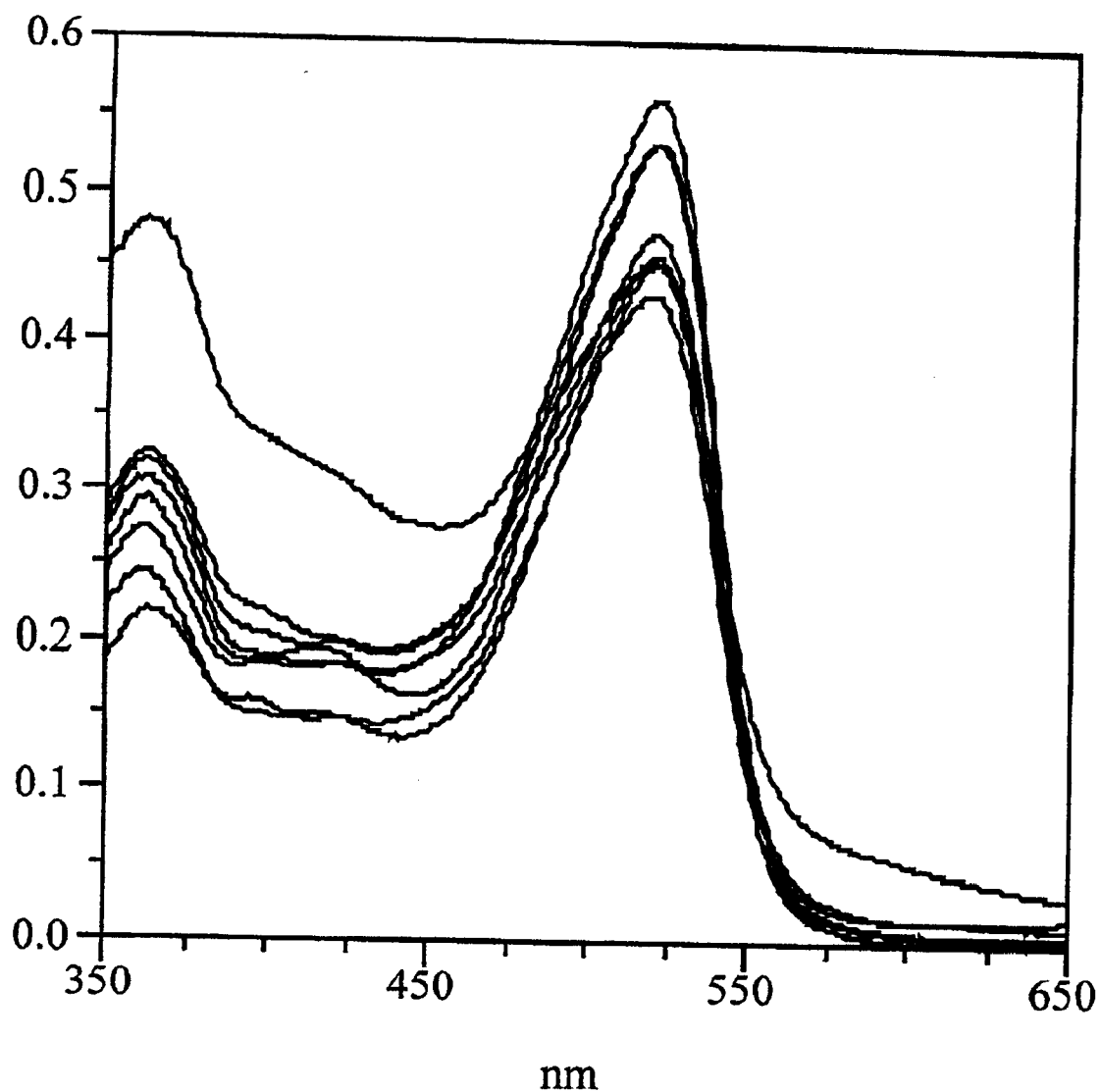
FIG. 9. Absorbance spectra for eight serum samples with LDL-C values equal to 169 mg/dL. Differences throughout the spectrum, and particularly in the 370–480 nm range, correlate with the relative amounts of PUFA's in the form of triglycerides and phospholipids. Spectra for subjects that are diabetic show a low maximum absorbance around 420 nm.

(23) A collection of these spectral snapshots measured for a broad representative cross section of the population at large, will serve as the basis library set for an entirely new approach to deriving prediction models for the early detection of dyslipidemias, coronary artery disease, and diabetes (FIG. 9). All of the subjects whose spectra appear in FIG. 9 had LDL-C values equal to 169 mg/dL. The variabilities are accountable by changes in the other lipoprotein cholesterol values and the differences in the PUFA contents of TG and PL.

(24) The fact that these same targeted unsaturated centers are labile to oxidation, the same basis set of raw spectral data in (23) could also be used in a new approach to deriving prediction models for the early detection of oxidative stress.

Figure 10:
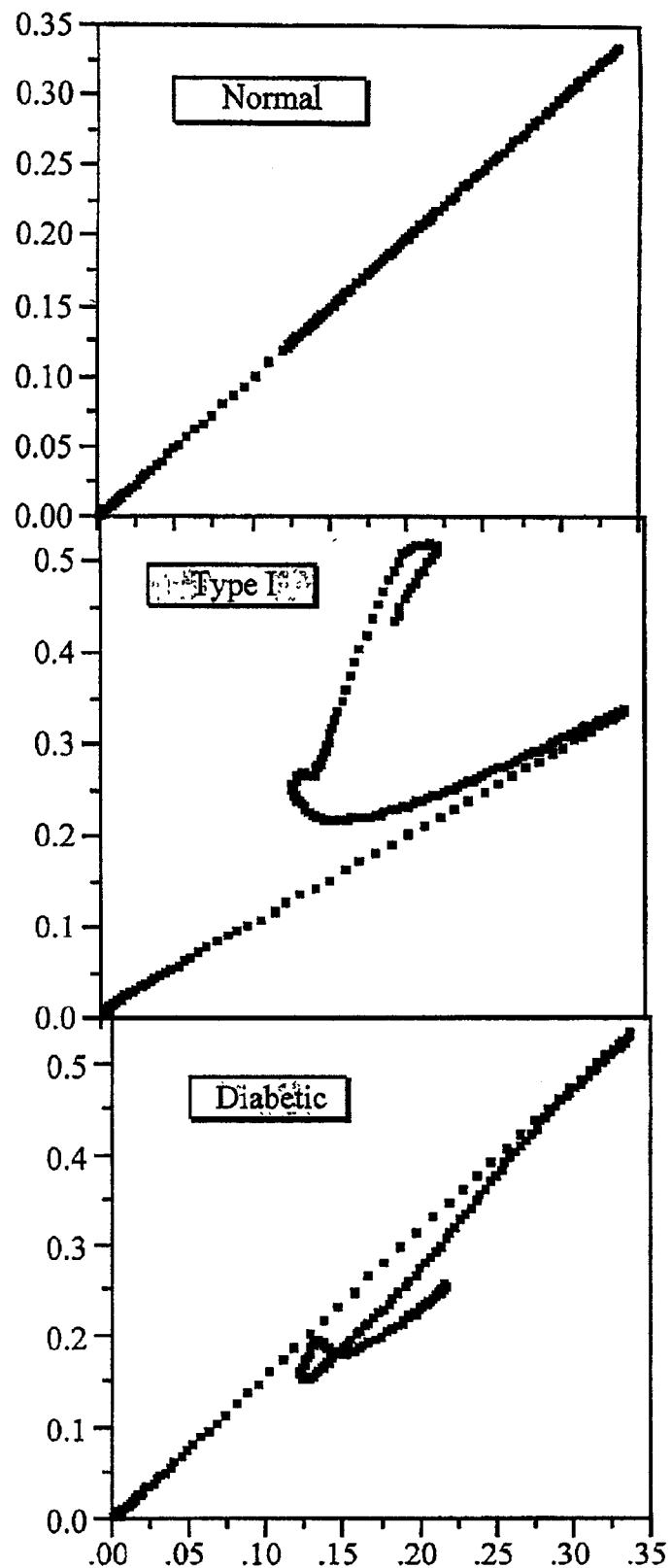
FIG. 10. Full spectrum cross-correlation plots for: a normal serum vs. a second normal serum (top); the same normal serum vs. the serum for a Type I dyslipidemia subject (middle); the same normal serum vs. serum for a diabetic subject (bottom).

(25) As a first test of (23), full spectral data from exploratory clinical trials on 94 subjects demonstrated that direct pair-wise 2-D cross correlations do exist between raw spectral data and serum dyslipidemias including diabetics (FIG. 10). Of the 94 subjects, 12 were evaluated as normal, 2 were Type I, 11 were Type IIa and IIb, 9 Type III, and 60 diabetics.

Figure 11:
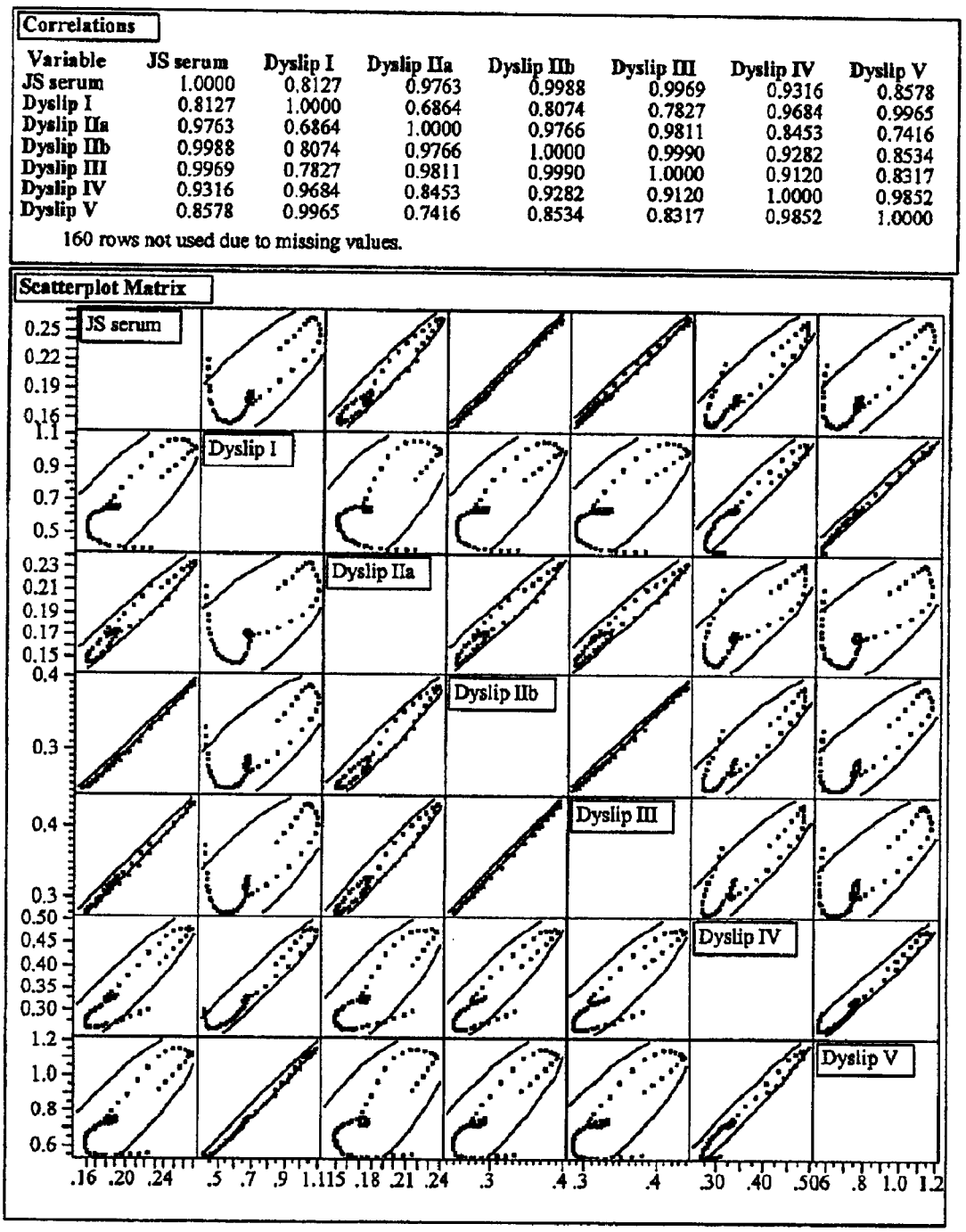
FIG. 11. A square matrix composed of a network of binary cross-correlation plots wherein 370–480 nm spectral data for each entry are simultaneously compared with all of the others. In making a preliminary diagnostic decision on a subject with unknown lipidemia, data are entered in the top left cell and cross-correlations are made against data for each type of dyslipidemia. The cell with the cross-correlation coefficient closest to 1.0 in the Variables Table is statistically the most likely diagnosis. In this particular example, the diagnosis is a Type IIb dyslipidemia.

(26) For a more general first step diagnosis, the spectrum for a subject with a suspected dyslipidemia can be added to a broad cross-correlation matrix diagram where it can be compared with representative spectra for all dyslipidemia types (FIG. 11). The best "diagnostic" match is derived from the matrix coordinates where the correlation variable is closest to 1.0. The sensitivity of the correlation variables are enhanced if the "full" spectral data are reduced to only the 360–480 nm wavelength range where the spectra of the cholesterol and PUFA analogs overlap.

(b) Statistically Treated Spectral Data

Figure 12:
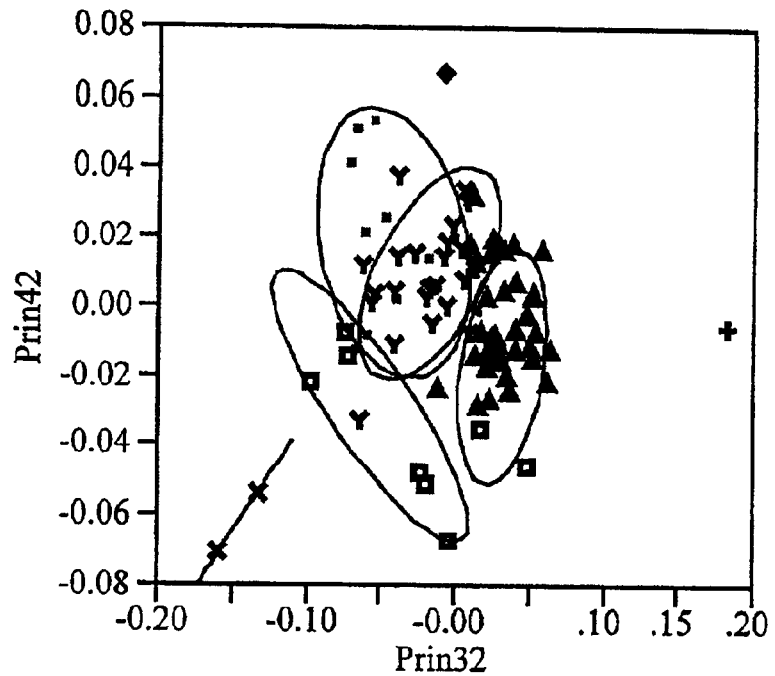
FIG. 12. Upper plot is a cluster diagram that correlates spectra for sera with similar lipids proportions in 2-D space. The coordinate axes are the two most sensitive principal components derived from a PCA of the spectral data from 360–480 nm. Different lipid types are identified by: Y (normal); X (Type I); small square (Type II); large open square (Type III); triangle (diabetic). Lower drawing is a spinning plot diagram that correlates the same spectra for the same sera in 3-D space and separates the "overlapping" clusters in the 2-D plot. Symbols used in the upper plot are repeated. The third axis is the third most sensitive principal component.
Figure 12:
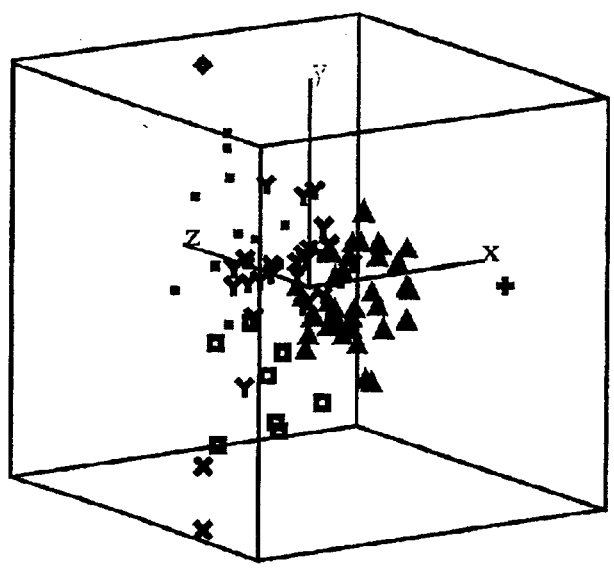

(27) The raw spectral data for the limited wavelength range in (26) for the same 94 subjects in (25) were subjected to tests using multivariate principal component analysis (PCA) algorithms. All 94 spectra, composed of 65 absorbance values, could be fitted by 8 principal components (PC's). By correlating the PC's in pairs or in triads, the relationships among all of the spectra could be simultaneously expressed in 2-D and 3-D clustering diagrams, (FIG. 12). The confidence level (perimeter) for the 2-D elliptical-clustering discriminations is set at 90%.

Correct correlations of points with particular lipidemia groupings are predicted for 9 of the 12 "normals"; 2 of 2 Type I; 9 of 11 Type II; 6 of 13 Type III, and 52 out of 60 diabetics, for a total correct assignment ratio of 78/96, or 81.3%. The success ratio is increased when the $3^{rd}$ dimension is added in the Spinning Plot presentation, (FIG. 12). The $3^{rd}$ dimension shows the spatial (along the z-axis) separation of clusters that appear to overlap in 2-D where all the clusters are projected on to an x-y plot. A caveat in regard to the data treatment as it is presented in the FIGS. (10–12) is the fact that a few Type II and Type III patients were already on lipid-lowering drug treatments at the times the samples were collected. Predictions for these patients, therefore are skewed towards the "normal" lipidemia grouping. With better control of patient selection higher success rates are anticipated.

This diagnostic procedure is unique in that the usual variables TC, TG, VLDL-C, LDL-C, and HDL-C are not involved in any way in arriving at "diagnostic" predictions.

Cholesterol and Serum Lipoproteins

(28) Resorting to the more common practice of measuring lipoprotein cholesterol profiles, VLDL1-C, VLDL2-C, IDL-C, LDL-C, and HDL-C, were determined spectroscopically for 36 subjects using artificial neural networking (ANN) algorithms to treat absorbance data in the spectral range 350–480 nm. TC is calculated as the sum of the parts. All of the lipofraction cholesterols are measured directly and with equal accuracy and precision. To correlate these numbers with results from a conventional assay, the same cholesterol profiles were measured by sequential ultracentrifugation. Linear regression equations for correlations between methods are: y=0.993x+3.27 for TC; y=0.906x+0.83 for VLDL1-C; y=0.965x+1.62 for VLDL2-C; y=0.910x+2.30 for LDL-C; y=0.903x+4.75 for HDL-C.

(29) In this invention there is no apparent limit imposed by the serum TG level, of the Friedewald equation. Spectra for subjects whose TG values exceeded 3000 mg/dL are measured with equal precision.

(30) Because of (29), nowhere in the development of the procedures in (23–27) is any individual excluded in compiling an unbiased basis set for CHD risk prediction models which is in stark contrast to the limiting approximations imposed on TG (<400 mg/dL) and VLDL-C (=TG/5) in the Freidewald equation. Their inclusion means that any derived prediction models are not subject to arbitrary biases created by the selective exclusion of high risk patients.

(31) Because of (29), not one person would be disqualified when choosing a cohort from local, regional, national, or international community, because of an arbitrarily imposed upper limit on any blood component.

(32) Because of (29), conclusions from multivariate statistical analysis data treatments, such as ANN and principal component analysis (PCA), which are used in this invention, are not biased by the elimination of individuals at high risk.

(33) The combination of multiple wavelength detection and multivariate data analysis eliminates every need to physically separate serum lipoprotein fractions either by selective precipitation, based upon their relative densities, or by ultracentrifugation, based upon their relative flotation properties, e.g. the β-quantification method.

PUFA's in Reference Materials and in Natural Oils

(34) Statistically untreated spectra and PC-correlation plots have enough discriminatory power to distinguish between cis- and trans-geometrical isomers, between positional isomers, e.g. ω-3- and ω-6-linolenic acids, and between conjugated and unconjugated isomers. Being able to experimentally discriminate between conjugated and non-conjugated isomers of PUFA esters with equal numbers of C-atoms is an elementary procedure and provides for a new and important routine analytical method for their assays, either separately or in many component combinations (FIG. 6). The test has potential clinical significance in the measurement of oxidative stress.

Figure 13:
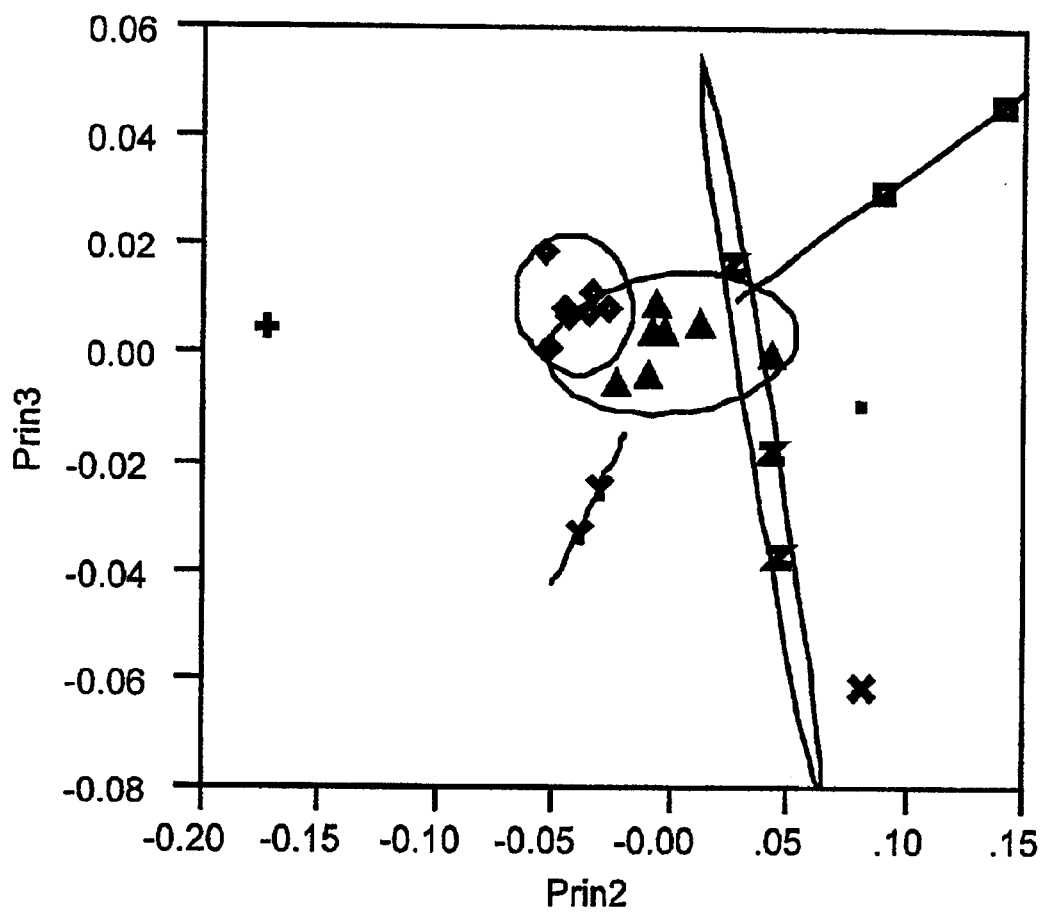
FIG. 13. Cluster diagram correlating spectra for PUFA's by their similar unsaturations. The diagram includes SRM's and natural oils. The coordinate axes are the two most sensitive PC's derived from a PCA of the spectral data from 360–480 nm in 10 nm increments. Isolated points are for conjugated methyl linoleate (+) and gamma-linolenate (X).

(35) A PCA of absorbance spectra measured with a 2 nm resolution from 350–750 nm for SRM's of PUFA's in the form of free acids, their cis- and trans-methyl esters, and glyceryl esters, combined with spectral data for pure samples of olive, soybean, safflower, sunflower, and fish oils reduces the full spectral data of 200 data points to only 8 principal components (PC's). 2-D and 3-D clusters made from the most significant PC's shows strong spectral correlations between the pure species and their presence in mixtures (FIG. 13). Any deviation from the clusters are clear evidence that a pure natural oil has been contaminated making this a probable quality control assay.

Synthetic Lipoproteins and Synthetic Dysplipidemias

(36) Absorbance spectra for solutions of synthetic lipoproteins prepared to mimic serum chylomicrons, VLDL, IDL, LDL, and HDL particles using literature values for the relative amounts of FC, its saturated and unsaturated esters, triolein and triolenin as TG mimics, and egg lecithin to mimic PL, correlate very well with experimentally measured data.

(37) Absorbance spectra for solutions of synthetic dyslipidemias prepared to mimic Types I, IIa, IIb, III, IV, and V, prepared by mixing synthetic lipoproteins from (36) according to published literature proportions, correlate very well with spectra measured for serum samples that were clinically confirmed to be from each type.

These 37 items constitute a compendium of original aspects that are associated with the invention. These aspects cover the general choice of the derivatization reagent of which there are several; the necessary structural properties of the analytes that are susceptible to the selected reagents; the spectral properties of the colored products from reactions with both SRM's and with mixtures of various lipids; interpretations of spectral data by the application of multivariate statistical analyses methods that include artificial neural networking, principal component analysis, and 2-D and 3-D clustering correlation algorithms; and how the whole package can be applied to (1) the diagnoses of lipids related disease states, (2) to the development of prediction models for heart disease and oxidative stress, (3) to the assay of natural oils and vitamins and, (4) to the analytical distinction among the various isomeric forms of PUFA's.

DETAILED PROCEDURE FOR THE ASSAY

The preferred binary and ternary reagent solutions are prepared in situ. For Bronsted acid reagents, the volume ratio of acid to acylating agents is 1:40. Although it can be added in solution, the Lewis acid Zn salts are better added as a weighed aliquot such that the ratio of acid to acylating agent is again approximately 1:40. Small variations from the exact numbers are permissible from one reagent to another in order to optimize the relative absorbance intensities of the color(s) and to enhance the discriminations among analytes. Volume ratios of acylating agents to modifier additive are dictated by the mutual solubilities the solvents involved and by the quality of the spectra and can be varied over the range 1/4 to 4/1.

For the color reaction, 1.0 mL of the acylating agent is added to a 10–25 $\mu$L aliquot of fasting serum or oil sample. Precipitated materials, when they occur, are separated either by low speed centrifugation or by filtration depending upon the reagent mix. The supernate is transferred to a 10 mm pathlength cuvet and the absorbance spectrum measured over the visible wavelength range 350–800 nm using a rapid scanning, preferably diode-array, spectrophotometer. The spectrum for reagent without added serum is used for the baseline correction. A diode-array instrument is almost mandatory if spectra are measured at one minute intervals over the development time to acquire kinetic information because spectral acquisition times are on the order of 5 seconds and can be automated. An alternative to separating the precipitate is to use simultaneous dual scan wavelength detection which factors out scattered light from suspended particles. Onset of color begins immediately the acid catalyst is added and continues rapidly with full development occurring within 8–15 minutes depending upon (a) the choice, and (b) the proportions of the components employed in preparing the reagent. When batching samples for assay, care must be taken to ensure that the final color is stable beyond the endpoint time. Reactions that might continue after the endpoint involve sera where TC and TG are very high. In those cases the addition of 10–25 $\mu$L of GAC at the prescribed endpoint will bring the reaction to an immediate stop, a function that is necessary if fluorescence is the detector of choice.

Factors in the assay are the ratios of sample to acylating agent to acid catalyst. This description, as it is written here, is based upon a 10 mm pathlength, narrow window, cuvet configuration. Temperature control is not a requirement. Absorbance maxima, measured at 360 nm and 520 nm, range from 0.25 to 1.5 absorbance units. Quantities can be reduced in size to satisfy different instrumental configurations, reduce the cost per sample, and alleviate disposal of the spent reagent. To preserve the 0.25–1.5 absorbance range, concentrations may have to be increased to accommodate a shorter pathlength, but reagent ratios should be maintained. Reagents are disposed of in water or dilute alkali solution Spectral data are archived in computer files. Data treatments involve multivariate statistical analysis software packages. Diagnostic correlation procedures rely upon clinical information and data measured independently and done according to standard reference procedures. Many software programs are commercially available to handle the specifics of the analyses.

TABLE 1

| Serum lipid | Wavelengths of band maxima | Relative intensities |
| --- | --- | --- |
| Cholesterol | 520 nm | Strong |
|  | 362, 404, 420(sh) nm | Moderately weak |
| Cholesteryl esters (satd.) | 520 nm | Strong |
|  | 362, 402(sh), 420 nm | Moderately weak |
| Cholesteryl linolenate | 520 nm | Strong |
|  | 362, 402(sh), 420 nm | All moderately weak |
| Cholesteryl linolenate | 520 nm | Strong |
|  | 362, 406(sh), 424(sh), 440 nm | All moderately weak |
| Cholesteryl arachidonate | 524 nm | Strong |
|  | 364, 400(sh), 420, 446(sh) nm | Diminishing with nm |
| Methyl 9,12-linoleate (unconjugated) | 358(sh), 372 nm | Strong |
|  | 422 nm | Moderately strong |
| Gamma methyl 9,12-linoleate | 370, 408(sh) nm | Strong |
|  | 430, 444(sh), 482 | Moderately strong |
| Methyl 9,11-linoleate (conjugated) | 360(sh), 372 nm | Strong |
| Methyl 10,12-linoleate (conjugated) | 412(sh), 430, 450(sh) | Strong |
| Methyl linolenate | 372, 402(sh) nm | Strong |
|  | 426, 444(sh), 486(sh) nm | Moderately strong |
| Glycerol trilinoleinate | 358(sh), 372 nm | More intense than |
|  | 422 nm | methyl ester |
| Glycerol trilinolenate | 372, 402(sh) nm | More intense than |
|  | 426, 444(sh), 486(sh) nm | methyl ester |
| Methyl arachidonate | 375, 422 nm | Very strong |
|  | 490(sh), 528(sh) 480(sh), 528(sh) | Weaker shoulders |
| Methyl eicosopentaenoate | 376, 422(sh), 444(sh), 488(sh), | Very strong |
|  | 516(sh), 560(sh) nm | Diminishing with nm |
| Methyl docosohexaenoate | 376, 422(sh), 444(sh), 486(sh), | Very strong |
|  | 512(sh), 540(sh), 562(sh) nm | Diminishing with nm |

While the invention has been described with a certain degree of particularity, it is manifest that many changes may be made in the method without departing from the spirit and scope of this disclosure. It is understood that the invention is not limited to the embodiment set forth herein for the purpose of exemplification, but is to be limited only by the scope of the attached claim or claims, including the full range of equivalency to which each step or element thereof is entitled.

What is claimed is:

1. A procedure for the simultaneous, comprehensive assay of unsaturated cyclic and open chain aliphatic molecular structures in a serum sample, comprising:

(a) simultaneously acylating said structures using a chromogenic reagent in a color reaction to obtain an acylated sample containing analogs of said structures;

(b) measuring spectral characteristics of said sample over substantially the entire visible wavelength range to obtain multiplexed spectral data; and (c) developing a comprehensive serum lipids profile discriminating among serum cholesterol and at least one of the group consisting of free unsaturated long chain fatty acids (LCFA's), saturated and unsaturated cholesteryl-LCFA esters, and LCFA's in the form of triglycerides and phospholipids, by comparing said multiplexed spectral data with characteristics representative of known concentrations of said analogs.

2. The procedure of claim 1, further comprising:

(d) comparing said profile to a library of data representative of normal and abnormal values to diagnose or evaluate risk factors for disease.

3. The procedure claim 2, wherein step (d) includes:

comparing said profile to data representative of Type I, IIa, IIb, III, IV and V dyslipidemias.

4. The procedure of claim 2, wherein the disease is diabetes.

5. The procedure of claim 2, wherein the disease is coronary artery disease.

6. The procedure of claim 1, wherein step (b) includes:

measuring the relative absorbance intensity of each analog in the acylated sample.

7. The procedure of claim 1, wherein step (b) includes:

measuring the relative fluorescence of each analog in the acylated sample.

8. The procedure of claim 1, wherein step (b) includes:

measuring the spectral characteristics using circular dichroism.

9. The procedure of claim 1, wherein step (c) includes:

discriminating among chylomicron, VLDL, DL, LDL and HDL lipoprotein fractions and subfractions.

10. The procedure of claim 1, wherein step (a) further comprises the substep of:

(a)(1) after a predetermined time, eliminating further progress of said color reaction.

11. The procedure of claim 10, wherein step (a)(1) includes:

adding at a predetermined time an amount of glacial acetic acid sufficient to stop said color reaction.

12. The procedure of claim 1, wherein step (b) further comprises the substep of:

(b)(1) repeating step (b) at short time intervals after step (a) up to and including the end point of the color reaction in order to produce kinetic spectral data.

13. The procedure of claim 1, wherein said chromogenic reagent is selected from the group consisting of acetyl chloride, acetic anhydride and glacial acetic acid and said color reaction is catalyzed by the addition of an acid selected from the group consisting of perchloric acid, zinc perchlorate hexahydrate, concentrated sulfuric acid, methanesulfonic acid and zinc organic acid salts.

14. The procedure of claim 13, wherein said chromogenic reagent is acetyl chloride and said color reaction is catalyzed by the addition of a 70% perchloric acid solution.

15. The procedure of claim 13, wherein said chromogenic reagent is acetyl chloride and said color reaction is catalyzed by the addition of a zinc perchlorate hexahydrate.

* * * * *

UNITED STATES PATENT AND TRADEMARK OFFICE
CERTIFICATE OF CORRECTION

PATENT NO. : 6,737,275 B2
DATED : May 18, 2004
INVENTOR(S) : Purdie et al.

It is certified that error appears in the above-identified patent and that said Letters Patent is hereby corrected as shown below:

Column 13,
Line 29, should read -- 3. The procedure of claim 2, wherein step (d) includes: --

Column 14,
Line 8, should read -- discriminating among chylomicron, VLDL, IDL, LDL and --

Signed and Sealed this

Tenth Day of May, 2005

JON W. DUDAS
*Director of the United States Patent and Trademark Office*